United States Patent [19]
Tuke

[11] Patent Number: 5,824,104
[45] Date of Patent: Oct. 20, 1998

[54] MENISCAL KNEE PROSTHESIS HAVING BOLLARD AND MOORING ATTACHMENT MEANS

[75] Inventor: Michael Antony Tuke, Guildford, United Kingdom

[73] Assignee: Finsbury (Instruments) Limited, Leatherhead, United Kingdom

[21] Appl. No.: 841,895

[22] Filed: Apr. 17, 1997

[30] Foreign Application Priority Data

Apr. 17, 1996 [GB] United Kingdom ............... 9607927

[51] Int. Cl.⁶ .................................................... A61F 2/38
[52] U.S. Cl. .......................................... 623/20; 623/18
[58] Field of Search ................................. 623/20, 18, 16

[56] References Cited

U.S. PATENT DOCUMENTS

| | | | |
|---|---|---|---|
| 3,946,445 | 3/1976 | Bentley et al. | 3/1.91 |
| 4,340,978 | 7/1982 | Buechel et al. | 623/20 |
| 4,353,136 | 10/1982 | Polyzoides et al. | 3/1.911 |
| 4,711,639 | 12/1987 | Grundei | 623/20 |
| 4,714,475 | 12/1987 | Grundei et al. | 623/20 |
| 4,728,332 | 3/1988 | Albrektsson | 623/20 |
| 4,770,663 | 9/1988 | Hanslik et al. | 623/20 |
| 4,795,468 | 1/1989 | Hoddrek et al. | 623/20 |
| 4,883,488 | 11/1989 | Bloebaum et al. | 623/20 |
| 4,959,071 | 9/1990 | Brown et al. | 623/20 |
| 5,007,932 | 4/1991 | Bekki et al. | 623/18 |
| 5,282,868 | 2/1994 | Bahler | 623/20 |
| 5,314,479 | 5/1994 | Rockwood et al. | 623/19 |

FOREIGN PATENT DOCUMENTS

| | | |
|---|---|---|
| 0 183 670 | 6/1986 | European Pat. Off. . |
| 0 349 173 | 1/1990 | European Pat. Off. . |
| 0 674 887 | 10/1995 | European Pat. Off. . |
| 1 534 263 | 11/1978 | United Kingdom . |
| 95/30390 | 11/1995 | WIPO . |

OTHER PUBLICATIONS

Brochures by BIOMET, Ltd., "Oxford Meniscal Knee Phase II, Components, Principles, Implant Listing, Theory of the Operation, Instrumentation, Choice of Patient, Theory of the Operation and price list", 4 pages, no date.

*Primary Examiner*—Michael J. Milano
*Assistant Examiner*—Tram Anh T. Nguyen
*Attorney, Agent, or Firm*—Senniger, Powers, Leavitt & Roedel

[57] ABSTRACT

An endoprosthetic knee comprising a tibial plate having a smooth proximal face and a distal face, an anchor on the distal face for anchoring the plate to the proximal end of a resected tibia, and at least one bollard on the proximal face of the tibial plate. At least one unicompartmental meniscal component has a substantially flat distal face for glidable seating on the tibial plate and a dished proximal face for receiving an articulating condylar surface of a femoral component anchorable to the distal end of a resected femur. A flexible mooring moors the meniscal component to the bollard on the tibial plate to permit limited gliding movement of the meniscal component upon the tibial plate.

14 Claims, 2 Drawing Sheets

MENISCAL KNEE PROSTHESIS HAVING BOLLARD AND MOORING ATTACHMENT MEANS

BACKGROUND OF THE INVENTION

The present invention relates to meniscal knee prostheses.

Conventionally, two principal types of endoprosthetic knee are known. The first type, the so-called total knee, comprises a tibial plate and a femoral component with an intervening meniscal component, each component having medial and lateral sides. Typically the tibial plate and femoral compartment are made from a suitable metal or metal alloy, such as an alloy of cobalt and chromium, whereas the meniscal components are made from a synthetic plastics material, for example ultra high molecular weight polyethylene. In most designs the meniscal component is fixed to the tibial plate. In other designs it is free to float to a certain extent with respect to the tibial plate in order that the prosthesis shall mimic better the natural movement of the knee. The total knee is designed to replace all of the articulating surfaces of the knee.

The second type of endoprosthetic knee, the so-called unicompartmental knee, also has a tibial plate, a femoral component and an intervening meniscal component. However, in this case, only a medial or, alternatively, a lateral femorotibial replacement is provided. Again it is usual for the meniscal component to be fixed to the tibia but in some designs there is provided a certain floating movement of the meniscal component.

A third type of endoprosthetic knee, referred to herein as the "bi-unicompartmental" type comprises two unicompartmental knee prostheses used, one on each of the lateral and medial sides, to replace all of the articulating surfaces of the femoro-tibial articulation.

In a variation on the total knee prosthesis, it is possible to have a single tibial plate with medial and lateral portions upon which are seated two separate meniscal components, one meniscal component upon each of the respective medial and lateral portions of the tibial plate.

When using a total knee replacement, it is possible for a surgeon to retain the patient's posterior cruciate ligament which can be accommodated within a cut-out portion in the centre of the posterior part of the tibial plate. However, it is not usually practical, when using this type of knee replacement, to preserve the anterior cruciate ligament, should this be intact. In order to accommodate the anterior cruciate ligament, the cut-out portion in the tibial plate has to be of such magnitude that the integral strength of the tibial plate is weakened beyond that which is acceptable.

The unicompartmental knee prosthesis generally requires that both posterior and anterior cruciate ligaments are retained by the surgeon, the knee being otherwise essentially normal.

There is a desire amongst surgeons working in this field to preserve the patient's anterior cruciate ligament if possible. Accordingly, in some indications, surgeons have made use of two unicompartmental prostheses to replace the total knee prosthesis. However, unicompartmental and "bi-unicompartmental" knee prostheses have suffered from certain disadvantages which have rendered them unpopular except in very specific indications.

One of the problems experienced by the unicompartmental and "bi-unicompartmental" meniscal knee prostheses is that the meniscal component has a tendency to slip out of the articulation between femur and tibia in some circumstances, causing locking of the knee and extreme pain to the patient.

One conventional meniscal knee addresses this problem to a certain extent by providing a non-round meniscal component with a high anterior lip that is controlled rotationally by a raised lip running the length of the edge of the tibial component adjacent the tibial eminence, against which the meniscal component abuts. The meniscal component is thereby afforded a degree of freedom of movement such as is necessary to mimic the range of motion of the human knee but is also constrained so as not to rotate across the sagittal plane of the knee.

However, this type of prosthesis is still not immune from dislocation and has remained somewhat unpopular for this reason. Despite its prolonged availability, its use as a "bi-unicompartmental" knee has remained very rare, surgeons preferring to use this type of prosthesis as a unicompartmental knee only.

SUMMARY OF THE INVENTION

It is therefore an object of the present invention to provide an improved meniscal unicompartmental, "bi-unicompartmental", or total knee for use in knee arthroplasty.

According to the present invention there is provided an endoprosthetic knee comprising:

a tibial plate having a smooth proximal face and a distal face, anchoring means on the distal face for anchoring the plate to the proximal end of a resected tibia, and at least one bollard means on the proximal face of the tibial plate;

at least one unicompartmental meniscal component having a substantially flat distal face for glidable seating on the tibial plate and a dished proximal face for receiving an articulating condylar surface of a femoral component anchorable to the distal end of a resected femur; and flexible mooring means for mooring the meniscal component to the bollard means on the tibial plate to permit limited gliding movement of the meniscal component upon the tibial plate.

Preferably, the meniscal component is arranged to be fully congruent with the femoral component.

Preferably the proximal face of the tibial plate is polished so as to facilitate movement of the meniscal component thereon.

The endoprosthetic knee of the invention is a compartmentalised endoprosthetic knee. It may be a unicompartmental knee. This allows only one side of the femoro-tibial joint to be replaced. An advantage of a unicompartmental knee according to the invention is that the surgeon is not required to sacrifice the patient's anterior cruciate ligament, should this ligament be sufficiently intact. A further advantage of such a unicompartmental knee is that it allows, in use, a degree of subluxation of the joint owing to the glidable movement of the meniscal component upon the tibial plate. However, whilst a degree of subluxation is permitted, luxation or excessive subluxation is prevented by the mooring line which moors the meniscal component to the tibial plate, thus limiting its range of gliding movement. The facility of a degree of subluxation with minimal danger of luxation or excessive subluxation is a particularly advantageous feature of endoprosthetic knees according to the invention. In this regard, the endoprosthetic knee mimics the full range of motion of the human knee, in which a degree of subluxation is possible because of the resilience of the semilunar fibrocartilages on the proximal tibia. Yet another advantageous feature of a unicompartmental endoprosthetic knee in accordance with the invention is that knee arthroplasty using such an endoprosthesis is less invasive than in conventional knee arthroplasty for most indications, in which total knee endoprostheses are generally used.

It is preferred that in a unicompartmental endoprosthetic knee according to the present invention the gliding movement of the meniscal component upon the tibial plate includes a degree of rotation of the meniscal component, about the axis of the tibia upon the tibial plate, of up to about 20° in total.

An advantageous feature of an endoprosthetic knee in accordance with the invention is that the patient can expect, after knee arthroplasty, to have an improved range of movement in the joint in comparison with conventional unicompartmental knees, but with a significant reduction in the corresponding danger of dislocation and associated pain and in the risk of need for further surgery.

Preferably, in a unicompartmental endoprosthetic knee in accordance with the invention, the gliding movement of the meniscal component upon the tibial plate includes a degree of rectilinear slippage in an anterior-posterior direction, preferably of not more than about 8 mm. It is further preferred that the gliding movement of the meniscal component upon the tibial plate includes a degree of rectilinear slippage in a medial-lateral direction, preferably of not more than about 4 mm. Advantageously for the user, true congruency can be maintained between the meniscal component and the femoral component whilst a degree of subluxation is still afforded by the gliding movement of the meniscal component upon the tibial plate. Accordingly, because of the freedom of movement provided to the user by the prosthesis of the invention, it is possible for the meniscal component thereof to be arranged to receive a corresponding femoral component with true congruency. True congruency between the femoral and meniscal components reduces the amount of wear of the meniscal component and increases its working life compared to those conventional prostheses in which true congruency is not maintained. It is also an advantage that materials other than plastic may be used. For example, all components of the prosthesis may be manufactured from cobalt chrome alloy (i.e. femur, tibia and menisci of a uni, total or bi-unicompartmental knee prosthesis).

The endoprosthetic knee of the invention may alternatively be designed as a "bi-unicompartmental" knee prosthesis. Thus the invention further provides an endoprosthetic knee comprising:

a first tibial plate having a smooth proximal face and a distal face, anchoring means on the distal face for anchoring the plate to the lateral side of the proximal end of a resected tibia, and first bollard means on the proximal face of the first tibial plate;

a second tibial plate having a smooth proximal face and a distal face, anchoring means on the distal face for anchoring the plate to the medial side of the proximal end of the resected tibia, and second bollard means on the proximal face of the second tibial plate;

a first meniscal component having a substantially flat distal face for glidable seating on the first tibial plate and a dished proximal face for receiving an articulating surface of a first condyle of a femoral component anchorable to the distal end of a resected femur;

a second meniscal component having a substantially flat distal face for glidable seating on the second tibial plate and a dished proximal face for receiving an articulating surface of a second condyle of the femoral component;

first flexible mooring means for mooring the first meniscal component to the bollard means on the tibial plate to permit limited gliding movement of the meniscal component upon the tibial plate; and second flexible mooring means for mooring the second meniscal component to the bollard means on the tibial plate to permit limited gliding movement of the meniscal component upon the tibial plate.

An advantage of a "bi-unicompartmental" endoprosthetic knee according to the invention is that a surgeon may use the endoprosthesis when total knee arthroplasty is indicated but, nevertheless, the patient's anterior cruciate ligament is intact. Preservation of the anterior cruciate ligament in such indications has not hitherto been possible due to the impracticality of a total knee prosthesis accommodating the anterior cruciate ligament and to the unsatisfactory risks of dislocation associated with conventional "bi-unicompartmental" endoprosthetic knees. Another advantage of "bi-unicompartmental" endoprosthetic knees according to the invention is that the invasiveness of surgery required when total knee endoprosthesis is indicated may be reduced in comparison with conventional surgical methods in such indications.

The endoprosthetic knee of the invention may alternatively be designed as a total knee prosthesis. Thus the invention further provides an endoprosthetic knee comprising:

a tibial plate having a medial component and a lateral component, a smooth proximal face and a distal face, anchoring means on the distal face for anchoring the plate to the proximal end of a resected tibia, and bollard means on the proximal surface of the tibial plate;

a first meniscal component having a substantially flat distal face for glidable seating on the medial component of the tibial plate and a dished proximal face for receiving an articulating surface of a first condyle of a femoral component anchorable to the distal end of a resected femur;

a second meniscal component having a substantially flat distal face for glidable seating on the lateral component of the tibial plate and a dished proximal face for receiving an articulating surface of a second condyle of the femoral component; and flexible mooring means for mooring at least one of the first and second meniscal components to the bollard means on the tibial plate to permit limited gliding movement of the respective meniscal component upon the tibial plate.

In a preferred embodiment of the invention the flexible mooring means comprises a mooring line which passes around or is secured to the or a respective bollard means for mooring of a respective meniscal component to a bollard means on the tibial plate such that gliding movement of the respective meniscal component upon the tibial plate is limited by slack in or elasticity of the mooring line. Such a mooring line can be secured at its ends to the meniscal component. Both ends can be secured to the meniscal component at a single point or the ends of the mooring line can be secured at spaced points to the meniscal component. Alternatively the mooring line can form a closed loop which passes around the lateral periphery of the meniscal component. In this case the loop can be unattached either to the bollard means or to the meniscal component. Yet another possibility is to use a pair of mooring lines to moor the meniscal component to the bollard means. In the case of a "bi-unicompartmental" endoprosthetic knee or a total endoprosthetic knee according to the invention each meniscal component may have its own mooring line or set of mooring lines. Alternatively a single mooring line or set of mooring lines can be used to moor both meniscal components to the two bollard means.

A total endoprosthetic knee according to the invention has the advantage over conventional total knee endoprostheses art in that subluxation in the respective medial and lateral compartments of the knee is substantially independent of the other compartment. In this respect, articulation of a total endoprosthetic knee according to the invention reflects more closely than do conventional total knee endoprostheses the articulation of the natural knee, wherein subluxation in the medial and lateral compartments of the knee is independently facilitated by the resilience of the semilunar fibrocartilages on the tibial head.

Endoprosthetic knees according to the invention may comprise an edge groove in the meniscal component for receipt of the mooring line. Preferably, the edge groove is arranged to receive the mooring line as a snug fit to avoid slippage of the mooring line within the groove.

The bollard means may comprise a T-shaped bar having a stem around which the mooring line may be secured and a crosspiece to prevent slippage of the mooring line from the stem. In one convenient arrangement, the crosspiece is transversely offset with respect to the stem to facilitate attachment of the mooring line thereto.

It is also envisaged that an endoprosthetic knee according to the invention may comprise an abutment member on the proximal surface of the tibial plate, against which member the meniscal component abuts at the limit of its gliding movement upon the tibial plate. Conveniently, the bollard means comprises the abutment member.

The mooring line can be formed from any suitable material. A unifilamentary line may be used but it will normally be preferred to utilize braided cord, nylon, or polypropylene. The material may be natural or man made. It may be biologically active. Possible materials include Dacron™.

In order that the invention may be clearly understood and readily carried into effect, a number of specific embodiments thereof will now be described with reference to the accompanying drawings, in which:

BRIEF DESCRIPTION OF THE DRAWINGS

FIG. 1(*b*) shows a cross-section on line A—A of FIG. 1(*a*);

FIG. 1 (*c*) shows a cross-section on line B—B of FIG. 1 (*a*);

FIG. 2(*b*) shows a cross-section on line C—C of FIG. 2(*a*); and

FIG. 2(*c*) shows a cross-section on line D—D of FIG. 2*a*.

DETAILED DESCRIPTION OF THE PREFERRED EMBODIMENT

Figure 1A:
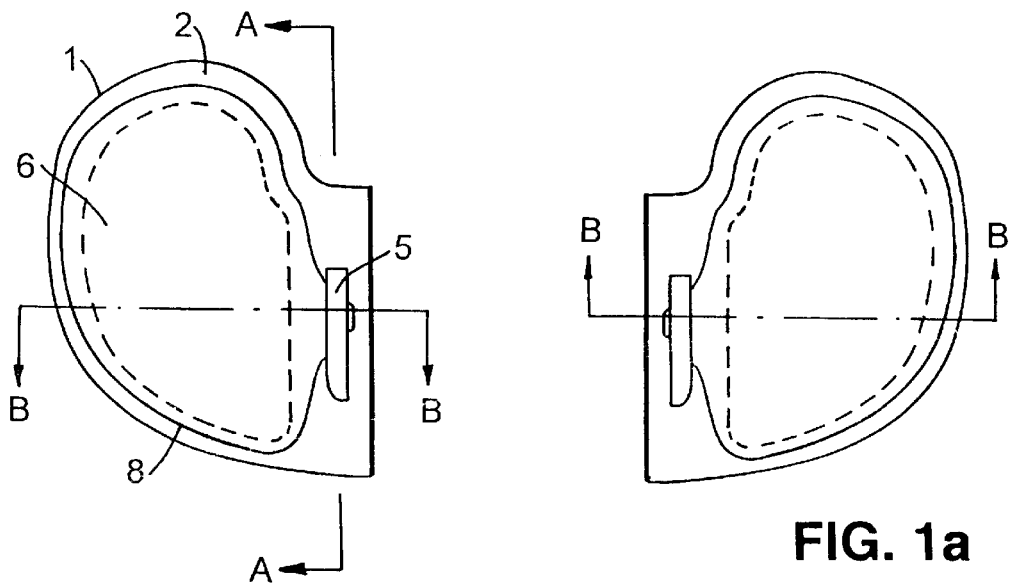
FIG. 1(*a*) shows a top plan view, partially in outline, of two mirror-image tibial plates and corresponding meniscal components of a first embodiment of the invention.
Figure 1B:
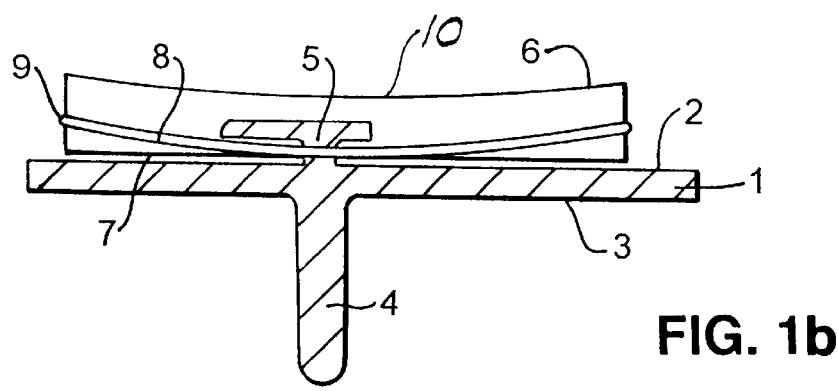
Figure 1C:
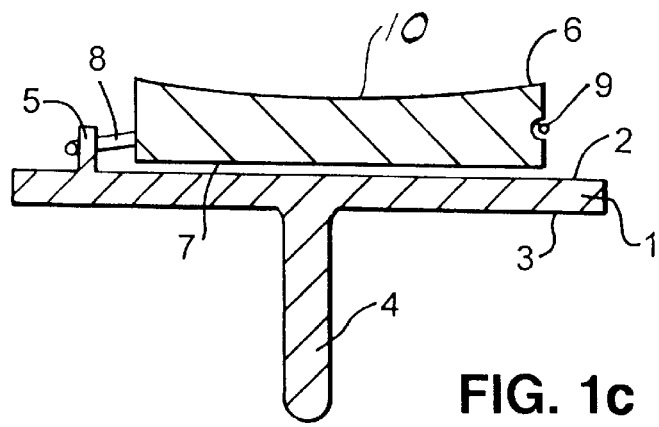

Referring to FIG. 1 there is shown a tibial plate 1 having a smooth proximal surface 2 and a distal surface 3. Tibial plate 1 comprises a longitudinal pin 4 extending from the distal face 3 of tibial plate 1, pin 4 being adapted for insertion into a longitudinal cavity drilled in the patient's tibia to anchor the tibial plate to the bone. Optionally, ancillary anchoring means may also be used. These may comprise one or more further pegs which may be ribbed for extra adhesiveness. In addition, distal face 3 may be dimpled to provide better adhesion to the bone surface. Such methods and means for anchoring the tibial plate to the bone are known and are well understood by those skilled in the art.

Upstanding from proximal surface 2 of tibial plate 1 is bollard member 5 which, as is best shown in FIG. 1(*b*), is a T-shaped bar in which the cross piece has been transversely offset with respect to the stem. Preferably, bollard member 5 and tibial plate 1 are of unitary construction. Tibial plate 1 is preferably made from an alloy of cobalt and chromium. The dimensions of tibial plate 1 may vary for different patients and/or for different indications. Particularly, the thickness of tibial plate 1 is normally from about 2mm to about 4mm.

Meniscal component 6 is seated on tibial plate 1 and is shown only in outline in FIG. 1(*a*). Meniscal component 6 has a substantially flat distal face 7 for glidable seating on proximal face 2 of tibial plate 1. Meniscal component 6 also has a dished proximal face 10 for receiving a femoral component (not shown). Meniscal component 6 may be constructed from ultra high molecular weight polyethylene. Alternatively, a metal component 6, for example of cobalt chromium alloy, may be used. The dimensions of the meniscal component may vary for different patients and/or indications. In particular, the thickness of the meniscal component is normally between about 5mm and 15mm at the thinnest point of the meniscal component.

Endoprosthetic knees according to the invention may be manufactured to fit various bone sizes. The combined thickness of the tibial plate and meniscal component together with the femoral component for use therewith may be chosen to match a particular flexion/extension gap which the surgeon has cut. Normally, femoral components which are commercially available are manufactured with a standard thickness of about 9 mm. The combined thickness of the tibial plate and meniscal component is preferably between about 7 mm and about 17 mm, for example 7 mm, 9.5 mm, 12 mm, 14.5 mm or 17 mm Mooring line 8 is a closed loop of braided cord or other suitable material which encircles meniscal component 6 around its edge and is looped around bollard member 5 so that gliding movement of meniscal component 6 upon tibial plate 1 is limited by slack in or elasticity of mooring line 8.

Medial component 6 accommodates mooring line 8 in an edge groove 9. Preferably, edge groove 9 is arranged to receive mooring line 8 as a snug fit to avoid slippage of mooring line 8 within edge groove 9.

Mooring line 8 may be formed as a closed loop. Alternatively, various other methods and means of attaching mooring line 8 to meniscal component 6 may be used. For example, holes through the meniscal compound may be used instead of a groove, and the line may be knotted to control its pull through. The surgeon should be able to assemble the chosen meniscal component to the bollard in such a way that it remains securely attached unless it is detached by the surgeon.

Figure 2A:
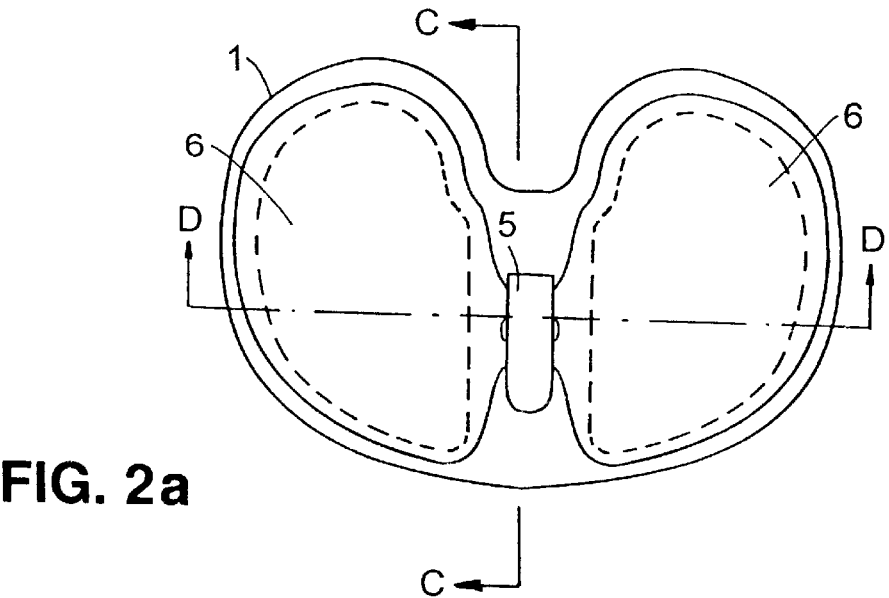
FIG. 2(*a*) shows a top plan view, partially in outline, of a tibial plate and corresponding meniscal components of a second embodiment of the invention.
Figure 2B:
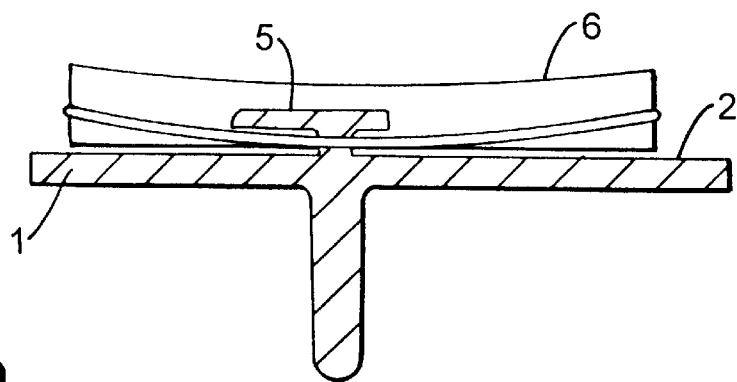
Figure 2C:
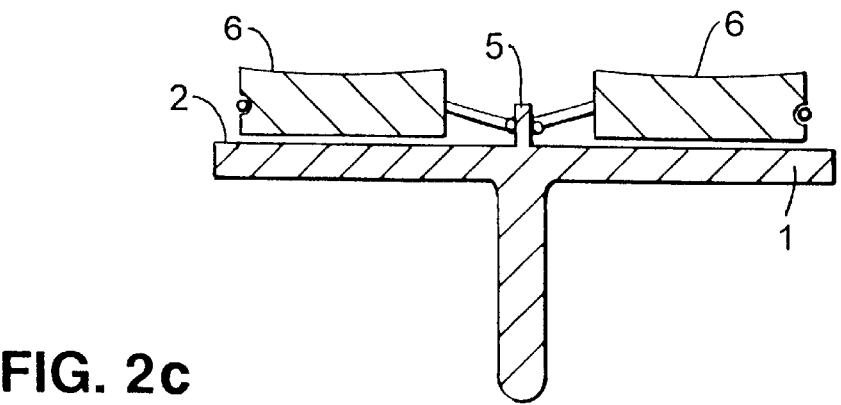

Referring to FIG. 2, there is shown tibial plate 1 having both medial and lateral components. On proximal surface 2 of tibial plate 1 there are seated two mirror-image meniscal components 6. Meniscal components 6 are both secured to bollard member 5 as previously described.

I claim:

1. An endoprosthetic knee comprising:
   a tibial plate having a smooth proximal face and a distal face, an anchor on the distal face for anchoring the tibial plate to the proximal end of a resected tibia, and a bollard on the proximal face of the tibial plate;

a unicompartmental meniscal component having a substantially flat distal face for glidable seating on the tibial plate and a dished proximal face for receiving an articulating condylar surface of a femoral component anchorable to the distal end of a resected femur; and a flexible mooring for mooring the meniscal component to the bollard on the tibial plate to permit limited gliding movement of the meniscal component upon the tibial plate.

2. An endoprosthetic knee as set forth in claim 1:

wherein the tibial plate constitutes a first tibial plate anchorable on the lateral side of the proximal end of a resected tibia;

the endoprosthetic knee further comprising a second tibial plate having a smooth proximal face and a distal face, an anchor on the distal face for anchoring the second tibial plate to the lateral side of the proximal end of a resected tibia, and a bollard on the proximal face of the second tibial plate;

wherein the unicompartmental meniscal component constitutes a first meniscal component associated with the first tibial plate, the dished proximal face of the first meniscal component being adapted to receive an articulating surface of a first condyle of the femoral component;

the endoprosthetic knee further comprising a second unicompartmental meniscal component having a substantially flat distal face for glidable seating on the second tibial plate and a dished proximal face for receiving an articulating surface of a second condyle of the femoral component;

wherein the flexible mooring constitutes a first flexible mooring for mooring the first meniscal component to the bollard on the first tibial plate;

the endoprosthetic knee further comprising a second flexible mooring for mooring the second meniscal component to the bollard on the second tibial plate to permit limited gliding movement of the second meniscal component upon the second tibial plate.

3. An endoprosthetic knee as set forth in claim 1:

wherein the tibial plate has a medial part and a lateral part, the bollard being on the medial part, the tibial plate further including another bollard on the lateral part of the tibial plate;

wherein the unicompartmental meniscal component constitutes a first meniscal component associated with the medial part of the tibial plate, the dished proximal face of the first meniscal component being adapted to receive an articulating surface of a first condyle of the femoral component;

the endoprosthetic knee further comprising a second unicompartmental meniscal component having a substantially flat distal face for glidable seating on the lateral part of the tibial plate and a dished proximal face for receiving an articulating surface of a second condyle of the femoral component;

wherein the flexible mooring constitutes a first flexible mooring for mooring the first meniscal component to the bollard on the medial part of the tibial plate;

the endoprosthetic knee further comprising a second flexible mooring for mooring the second meniscal component to the bollard on the lateral part of the tibial plate to permit limited gliding movement of the second meniscal component upon the lateral part of the tibial plate.

4. An endoprosthetic knee according to claim 1, wherein the gliding movement of the meniscal component upon the tibial plate includes a degree of rotation of the component upon the plate of up to about 20° in total.

5. An endoprosthetic knee according to claim 1, wherein the gliding movement of the meniscal component upon the tibial plate includes a degree of rectilinear slippage in an anterior-posterior direction of up to about 8 mm.

6. An endoprosthetic knee according to claim 1, wherein the gliding movement of the meniscal component upon the tibial plate includes a degree of rectilinear slippage in a medial-lateral direction of up to about 4 mm.

7. An endoprosthetic knee according to claim 1, wherein the meniscal component comprises an edge groove for attachment of the flexible mooring.

8. An endoprosthetic knee according to claim 7 wherein the edge groove is arranged to receive the flexible mooring as a snug fit to avoid slippage of the flexible mooring within the groove.

9. An endoprosthetic knee according to claim 1, wherein the meniscal component has at least one hole for receiving the flexible mooring.

10. An endoprosthetic knee according to claim 1, wherein the bollard comprises a T-shaped bar having a stem around which the flexible mooring may be secured and a crosspiece for preventing slippage of the flexible mooring from the stem.

11. An endoprosthetic knee according to claim 10, wherein the crosspiece is transversely offset with respect to the stem to facilitate attachment of the flexible mooring thereto.

12. An endoprosthetic knee according to claim 1, wherein the tibial plate further includes a limit surface positioned for engagement with the meniscal component at the limit of its gliding movement upon the tibial plate.

13. An endoprosthetic knee as set forth in claim 12 wherein the bollard defines the limit surface.

14. An endoprosthetic knee according to claim 1, wherein the flexible mooring is formed from Dacron™.

* * * * *